(12) United States Patent
Ryo et al.

(10) Patent No.: US 8,080,384 B2
(45) Date of Patent: Dec. 20, 2011

(54) METHOD FOR DETERMINATION OF PROGNOSIS OF PROSTATE CANCER, AND DIAGNOSTIC AGENT FOR USE IN THE METHOD

(75) Inventors: Akihide Ryo, Yokohama (JP); Ichiro Aoki, Yokohama (JP); Takeshi Sasaki, Yokohama (JP)

(73) Assignee: Yokohama City University, Yokohama-Shi (JP)

( * ) Notice: Subject to any disclaimer, the term of this patent is extended or adjusted under 35 U.S.C. 154(b) by 318 days.

(21) Appl. No.: 12/225,998

(22) PCT Filed: Mar. 30, 2007

(86) PCT No.: PCT/JP2007/057048
§ 371 (c)(1), (2), (4) Date: Oct. 3, 2008

(87) PCT Pub. No.: WO2007/119606
PCT Pub. Date: Oct. 25, 2007

(65) Prior Publication Data
US 2009/0305299 A1    Dec. 10, 2009

(30) Foreign Application Priority Data
Apr. 5, 2006  (JP) ................................. 2006-104315

(51) Int. Cl.
*G01N 33/574* (2006.01)

(52) U.S. Cl. ....................................... 435/7.23; 435/7.1
(58) Field of Classification Search .................. None
See application file for complete search history.

(56) References Cited

U.S. PATENT DOCUMENTS
2003/0073096 A1   4/2003   Bao et al.
2003/0153007 A1*  8/2003   Chen et al. ..................... 435/7.1

FOREIGN PATENT DOCUMENTS
JP   2002-511564 A   4/2002
JP   2004-532390 A  10/2004
WO   WO-99/42830 A1  8/1999

* cited by examiner

*Primary Examiner* — Misook Yu
*Assistant Examiner* — Mark Halvorson
(74) *Attorney, Agent, or Firm* — Birch, Stewart, Kolasch & Birch, LLP

(57) ABSTRACT

A method for determining probability that prostate cancer will metastasize, as well as a diagnostic reagent used therefor is disclosed. It was discovered that the percentage that NF-κB-p65/RelA has the 254th amino acid threonine which is phosphorylated is significantly higher in the prostate cancer cells in the cases where the bone metastasis was observed than in the cases where bone metastasis was not observed. Thus, the method for determining probability that prostate cancer will metastasize comprises measuring human NF-κB-p65/RelA in which 254th amino acid threonine is phosphorylated, which human NF-κB-p65/RelA is contained in a prostate tissue separated from human.

4 Claims, 1 Drawing Sheet

SEQUENCE LISTING

```
<160> NUMBER OF SEQ ID NOS: 3

<210> SEQ ID NO 1
<211> LENGTH: 1767
<212> TYPE: DNA
<213> ORGANISM: Homo sapiens
<220> FEATURE:
<221> NAME/KEY: CDS
<222> LOCATION: (80)..(1735)

<400> SEQUENCE: 1
gaattccggc gaatggctcg tctgtagtgc acgccgcggg cccagctgcg accccggccc        60 cgccccggg accccggcc atg gac gaa ctg ttc ccc ctc atc ttc ccg gca       112
                    Met Asp Glu Leu Phe Pro Leu Ile Phe Pro Ala
                      1               5                  10 gag cca gcc cag gcc tct ggc ccc tat gtg gag atc att gag cag ccc       160
Glu Pro Ala Gln Ala Ser Gly Pro Tyr Val Glu Ile Ile Glu Gln Pro
              15                  20                  25 aag cag cgg ggc atg cgc ttc cgc tac aag tgc gag ggg cgc tcc gcg       208
```

-continued

```
      Lys Gln Arg Gly Met Arg Phe Arg Tyr Lys Cys Glu Gly Arg Ser Ala
               30                  35                  40 ggc agc atc cca ggc gag agg agc aca gat acc acc aag acc cac ccc      256
Gly Ser Ile Pro Gly Glu Arg Ser Thr Asp Thr Thr Lys Thr His Pro
 45                  50                  55 acc atc aag atc aat ggc tac aca gga cca ggg aca gtg cgc atc tcc      304
Thr Ile Lys Ile Asn Gly Tyr Thr Gly Pro Gly Thr Val Arg Ile Ser
 60                  65                  70                  75 ctg gtc acc aag gac cct cct cac cgg cct cac ccc cac gag ctt gta      352
Leu Val Thr Lys Asp Pro Pro His Arg Pro His Pro His Glu Leu Val
                 80                  85                  90 gga aag gac tgc cgg gat ggc ttc tat gag gct gag ctc tgc ccg gac      400
Gly Lys Asp Cys Arg Asp Gly Phe Tyr Glu Ala Glu Leu Cys Pro Asp
                 95                 100                 105 cgc tgc atc cac agt ttc cag aac ctg gga atc cag tgt gtg aag aag      448
Arg Cys Ile His Ser Phe Gln Asn Leu Gly Ile Gln Cys Val Lys Lys
                110                 115                 120 cgg gac ctg gag cag gct atc agt cag cgc atc cag acc aac aac aac      496
Arg Asp Leu Glu Gln Ala Ile Ser Gln Arg Ile Gln Thr Asn Asn Asn
125                 130                 135 ccc ttc caa gtt cct ata gaa gag cag cgt ggg gac tac gac ctg aat      544
Pro Phe Gln Val Pro Ile Glu Glu Gln Arg Gly Asp Tyr Asp Leu Asn
140                 145                 150                 155 gct gtg cgg ctc tgc ttc cag gtg aca gtg cgg gac cca tca ggc agg      592
Ala Val Arg Leu Cys Phe Gln Val Thr Val Arg Asp Pro Ser Gly Arg
                160                 165                 170 ccc ctc cgc ctg ccg cct gtc ctt cct cat ccc atc ttt gac aat cgt      640
Pro Leu Arg Leu Pro Pro Val Leu Pro His Pro Ile Phe Asp Asn Arg
                175                 180                 185 gcc ccc aac act gcc gag ctc aag atc tgc cga gtg aac cga aac tct      688
Ala Pro Asn Thr Ala Glu Leu Lys Ile Cys Arg Val Asn Arg Asn Ser
                190                 195                 200 ggc agc tgc ctc ggt ggg gat gag atc ttc cta ctg tgt gac aag gtg      736
Gly Ser Cys Leu Gly Gly Asp Glu Ile Phe Leu Leu Cys Asp Lys Val
                205                 210                 215 cag aaa gag gac att gag gtg tat ttc acg gga cca ggc tgg gag gcc      784
Gln Lys Glu Asp Ile Glu Val Tyr Phe Thr Gly Pro Gly Trp Glu Ala
220                 225                 230                 235 cga ggc tcc ttt tcg caa gct gat gtg cac cga caa gtg gcc att gtg      832
Arg Gly Ser Phe Ser Gln Ala Asp Val His Arg Gln Val Ala Ile Val
                240                 245                 250 ttc cgg acc cct ccc tac gca gac ccc agc ctg cag gct cct gtg cgt      880
Phe Arg Thr Pro Pro Tyr Ala Asp Pro Ser Leu Gln Ala Pro Val Arg
                255                 260                 265 gtc tcc atg cag ctg cgg cgg cct tcc gac cgg gag ctc agt gag ccc      928
Val Ser Met Gln Leu Arg Arg Pro Ser Asp Arg Glu Leu Ser Glu Pro
                270                 275                 280 atg gaa ttc cag tac ctg cca gat aca gac gat cgt cac cgg att gag      976
Met Glu Phe Gln Tyr Leu Pro Asp Thr Asp Asp Arg His Arg Ile Glu
285                 290                 295 gag aaa cgt aaa agg aca tat gag acc ttc aag agc atc atg aag aag     1024
Glu Lys Arg Lys Arg Thr Tyr Glu Thr Phe Lys Ser Ile Met Lys Lys
300                 305                 310                 315 agt cct ttc agc gga ccc acc gac ccc cgg cct cca cct cga cgc att     1072
Ser Pro Phe Ser Gly Pro Thr Asp Pro Arg Pro Pro Pro Arg Arg Ile
                320                 325                 330 gct gtg cct tcc cgc agc tca gct tct gtc ccc aag cca gca ccc cag     1120
Ala Val Pro Ser Arg Ser Ser Ala Ser Val Pro Lys Pro Ala Pro Gln
                335                 340                 345 ccc tat ccc ttt acg tca tcc ctg agc acc atc aac tat gat gag ttt     1168
```

```
Pro Tyr Pro Phe Thr Ser Ser Leu Ser Thr Ile Asn Tyr Asp Glu Phe
        350                 355                 360 ccc acc atg gtg ttt cct tct ggg cag atc agc cag gcc tcg gcc ttg     1216
Pro Thr Met Val Phe Pro Ser Gly Gln Ile Ser Gln Ala Ser Ala Leu
    365                 370                 375 gcc ccg gcc cct ccc caa gtc ctg ccc cag gct cca gcc cct gcc cct     1264
Ala Pro Ala Pro Pro Gln Val Leu Pro Gln Ala Pro Ala Pro Ala Pro
380                 385                 390                 395 gct cca gcc atg gta tca gct ctg gca gcc cca gcc cct gtc cca         1312
Ala Pro Ala Met Val Ser Ala Leu Ala Ala Pro Ala Pro Val Pro
                    400                 405                 410 gtc cta gcc cca ggc cct cct cag gct gtg gcc cca cct gcc ccc aag     1360
Val Leu Ala Pro Gly Pro Pro Gln Ala Val Ala Pro Pro Ala Pro Lys
                415                 420                 425 ccc acc cag gct ggg gaa gga acg ctg tca gag gcc ctg ctg cag ctg     1408
Pro Thr Gln Ala Gly Glu Gly Thr Leu Ser Glu Ala Leu Leu Gln Leu
            430                 435                 440 cag ttt gat gat gaa gac ctg ggg gcc ttg ctt ggc aac agc aca gac     1456
Gln Phe Asp Asp Glu Asp Leu Gly Ala Leu Leu Gly Asn Ser Thr Asp
    445                 450                 455 cca gct gtg ttc aca gac ctg gca tcc gtc gac aac tcc gag ttt cag     1504
Pro Ala Val Phe Thr Asp Leu Ala Ser Val Asp Asn Ser Glu Phe Gln
460                 465                 470                 475 cag ctg ctg aac cag ggc ata cct gtg gcc ccc cac aca act gag ccc     1552
Gln Leu Leu Asn Gln Gly Ile Pro Val Ala Pro His Thr Thr Glu Pro
                    480                 485                 490 atg ctg atg gag tac cct gag gct ata act cgc cta gtg aca ggg gcc     1600
Met Leu Met Glu Tyr Pro Glu Ala Ile Thr Arg Leu Val Thr Gly Ala
                495                 500                 505 cag agg ccc ccc gac cca gct cct gct cca ctg ggg gcc ccg ggg ctc     1648
Gln Arg Pro Pro Asp Pro Ala Pro Ala Pro Leu Gly Ala Pro Gly Leu
            510                 515                 520 ccc aat ggc ctc ctt tca gga gat gaa gac ttc tcc tcc att gcg gac     1696
Pro Asn Gly Leu Leu Ser Gly Asp Glu Asp Phe Ser Ser Ile Ala Asp
    525                 530                 535 atg gac ttc tca gcc ctg ctg agt cag atc agc tcc taa gggggtgacg     1745
Met Asp Phe Ser Ala Leu Leu Ser Gln Ile Ser Ser
540                 545                 550 cctgccctcc ccagagcact gg                                            1767

<210> SEQ ID NO 2
<211> LENGTH: 551
<212> TYPE: PRT
<213> ORGANISM: Homo sapiens

<400> SEQUENCE: 2

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
```

-continued

```
            100                 105                 110
Phe Gln Asn Leu Gly Ile Gln Cys Val Lys Lys Arg Asp Leu Glu Gln
        115                 120                 125
Ala Ile Ser Gln Arg Ile Gln Thr Asn Asn Pro Phe Gln Val Pro
        130                 135             140
Ile Glu Glu Gln Arg Gly Asp Tyr Asp Leu Asn Ala Val Arg Leu Cys
145                 150                 155                 160
Phe Gln Val Thr Val Arg Asp Pro Ser Gly Arg Pro Leu Arg Leu Pro
                165                 170                 175
Pro Val Leu Pro His Pro Ile Phe Asp Asn Arg Ala Pro Asn Thr Ala
            180                 185                 190
Glu Leu Lys Ile Cys Arg Val Asn Arg Asn Ser Gly Ser Cys Leu Gly
        195                 200                 205
Gly Asp Glu Ile Phe Leu Leu Cys Asp Lys Val Gln Lys Glu Asp Ile
    210                 215                 220
Glu Val Tyr Phe Thr Gly Pro Gly Trp Glu Ala Arg Gly Ser Phe Ser
225                 230                 235                 240
Gln Ala Asp Val His Arg Gln Val Ala Ile Val Phe Arg Thr Pro Pro
                245                 250                 255
Tyr Ala Asp Pro Ser Leu Gln Ala Pro Val Arg Val Ser Met Gln Leu
            260                 265                 270
Arg Arg Pro Ser Asp Arg Glu Leu Ser Glu Pro Met Glu Phe Gln Tyr
        275                 280                 285
Leu Pro Asp Thr Asp Asp Arg His Arg Ile Glu Glu Lys Arg Lys Arg
        290                 295                 300
Thr Tyr Glu Thr Phe Lys Ser Ile Met Lys Lys Ser Pro Phe Ser Gly
305                 310                 315                 320
Pro Thr Asp Pro Arg Pro Pro Pro Arg Arg Ile Ala Val Pro Ser Arg
                325                 330                 335
Ser Ser Ala Ser Val Pro Lys Pro Ala Pro Gln Pro Tyr Pro Phe Thr
            340                 345                 350
Ser Ser Leu Ser Thr Ile Asn Tyr Asp Glu Phe Pro Thr Met Val Phe
        355                 360                 365
Pro Ser Gly Gln Ile Ser Gln Ala Ser Ala Leu Ala Pro Ala Pro Pro
    370                 375                 380
Gln Val Leu Pro Gln Ala Pro Ala Pro Ala Pro Ala Pro Ala Met Val
385                 390                 395                 400
Ser Ala Leu Ala Gln Ala Pro Ala Pro Val Pro Val Leu Ala Pro Gly
                405                 410                 415
Pro Pro Gln Ala Val Ala Pro Pro Ala Pro Lys Pro Thr Gln Ala Gly
            420                 425                 430
Glu Gly Thr Leu Ser Glu Ala Leu Leu Gln Leu Gln Phe Asp Asp Glu
        435                 440                 445
Asp Leu Gly Ala Leu Leu Gly Asn Ser Thr Asp Pro Ala Val Phe Thr
        450                 455                 460
Asp Leu Ala Ser Val Asp Asn Ser Glu Phe Gln Gln Leu Leu Asn Gln
465                 470                 475                 480
Gly Ile Pro Val Ala Pro His Thr Thr Glu Pro Met Leu Met Glu Tyr
                485                 490                 495
Pro Glu Ala Ile Thr Arg Leu Val Thr Gly Ala Gln Arg Pro Pro Asp
            500                 505                 510
Pro Ala Pro Ala Pro Leu Gly Ala Pro Gly Leu Pro Asn Gly Leu Leu
        515                 520                 525
```

```
Ser Gly Asp Glu Asp Phe Ser Ser Ile Ala Asp Met Asp Phe Ser Ala
        530                 535                 540

Leu Leu Ser Gln Ile Ser Ser
545                 550

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide fragment used as an immunogen

<400> SEQUENCE: 3

Val Phe Arg Thr Pro Pro Tyr Ala Asp Pro Ser Cys
1               5                   10
```

METHOD FOR DETERMINATION OF PROGNOSIS OF PROSTATE CANCER, AND DIAGNOSTIC AGENT FOR USE IN THE METHOD

TECHNICAL FIELD

The present invention relates to a method for determining probability that a prostate cancer will metastasize, and to a diagnostic reagent therefor.

BACKGROUND ART

In the U.S., prostate cancer has the highest prevalence among cancers in males. In Japan too, the prevalence of the prostate cancer is consistently increasing due to the change of lifestyle such as westernization of dietary life (Non-patent Literature 1). Since no specific symptoms are manifested in the early stage of prostate cancer, and since prostate cancer is often complicated with benign prostatic hyperplasia, the symptoms similar to those of benign prostatic hyperplasia, and dysuria, nocturia, urinary urgency and the like are found in some cases. Therefore, recently, even though no symptom is observed, most of prostate cancer is detected by measurement of PSA prostate-specific antigen in the blood in medical examination or health screening. Prostate cancer is characterized by high frequency of metastasis, and in some cases, advanced cancer is found because of low back pain due to bone metastasis (Non-patent Literature 2).

As the factor deciding the prognosis of prostate cancer, stage (in the following) thereof before surgery is important.
Stage A: cases where prostate cancer was accidentally found in surgery of benign prostatic hyperplasia or bladder cancer
Stage B: cases where the cancer is confined in the prostate
Stage C: cases where the cancer is not metastasized to other organs (such as bone, lymph node, lung and liver), but the cancer is exposed to the outside of the coating membrane (the membrane coating the periphery of prostate)
Stage D: cases where the cancer is metastasized to other organs such as bone and lymph node For the cases of Stage A to Stage C, basically, total extirpation of prostate is carried out. However, in a considerable number of cases, recurrence of the cancer within several years after the surgery is observed. Especially, refractoriness to hormone therapy and metastasis are important factors which aggravate the survival prognosis, so that to estimate these factors at an early stage has a great clinical significance in the selection of therapy or treatment of the patient. However, up to now, no molecular marker is known which enables to estimate the prognosis of prostate cancer, especially the metastasis thereof, at an early stage.

On the other hand, it is known that blockade of NF-κB (nuclear factor, NF)-κB activity, which is one of the transcription factors, inhibits angiogenesis, infiltration and metastasis in human prostate cancer (Non-patent Literature 3). More particularly, Non-patent Literature 3 discloses that when a mutated IκBα gene having an activity to inhibit NF-κB activity was introduced into metastatic human prostate cancer cells PC-3M and the cells were transplanted to nude mice, angiogenesis, infiltration and metastasis were inhibited in the group wherein NF-κB activity was reduced by the introduction of the mutated IκBα gene when compared with the group wherein the human prostate cancer cells PC-3M into which the mutated IκBα gene was not introduced were transplanted. Non-patent Literature 4 discloses that in prostate cancer cells, expression of NF-κB significantly occurs in the nuclei. Non-patent Literature 5 discloses that by the action of Pin1 which is a type of peptidyl-prolyl isomerase that specifically acts on the sequence of phosphorylated threonine or serine and subsequent proline, which sequence exists in a protein, on p65/RelA which is a subunit of NF-κB and in which the 254th amino acid threonine is phosphorylated, the binding of NF-κB-p65/RelA to IκBα that is an inhibition factor of NF-κB is inhibited, so that nuclear accumulation and stability of NF-κB-p65/RelA are increased and, in turn, the NF-κB activity is increased.

Non-patent Literature 1: Wakai K. Descriptive epidemiology of prostate cancer in Japan and Western countries Nippon Rinsho. 2005 February; 63(2):207-12.

Non-patent Literature 2: Loberg R D, Gayed B A, Olson K B, Pienta K J. A paradigm for the treatment of prostate cancer bone metastases based on an understanding of tumor cell-microenvironment interactions. J Cell Biochem. 2005 Oct. 15; 96(3):439-46.

Non-patent Literature 3: Huang S, Pettaway C A, Uehara H, Bucana C D, Fidler I J. Blockade of NF-kappaB activity in human prostate cancer cells is associated with suppression of angiogenesis, invasion, and metastasis. Oncogene. 2001 Jul. 12; 20(31):4188-97.

Non-patent Literature 4: Lessard L, Begin L R, Gleave M E, Mes-Masson A M, Saad F. Nuclear localisation of nuclear factor-kappaB transcription factors in prostate cancer: an immunohistochemical study. Br J Cancer. 2005 Oct. 31; 93(9):1019-23.

Non-patent Literature 5: Ryo A, Suizu F, Yoshida Y, Perrem K, Liou Y C, Wulf G, Rottapel R, Yamaoka S, Lu K P. Regulation of NF-kappaB signaling by Pin1-dependent prolyl isomerization and ubiquitin-mediated proteolysis of p65/RelA. Mol Cell. 2003 December; 12(6):1413-26.

DISCLOSURE OF THE INVENTION

Problems to be Solved by the Invention

An object of the present invention is to provide a method for determining probability that a prostate cancer will metastasize and a diagnostic reagent therefor.

Means for Solving the Problems

The present inventors intensively studied to discover that the percentage that NF-κB-p65/RelA has the 254th amino acid threonine which is phosphorylated is significantly higher in the prostate cancer cells in the cases where the bone metastasis was observed than in the cases where bone metastasis was not observed, and that the probability that a prostate cancer will metastasize can be determined at an early stage by examining whether the 254th amino acid threonine in NF-κB-p65/RelA is phosphorylated or not, thereby completing the present invention.

That is, the present invention provides a method for determining probability that a prostate cancer will metastasize, the method comprising measuring human NF-κB-p65/RelA in which 254th amino acid threonine is phosphorylated, the human NF-κB-p65/RelA being contained in a prostate tissue separated from human. The present invention also provides a diagnostic reagent for determining probability that a prostate cancer will metastasize, the reagent comprising an antibody or an antigen-binding fragment thereof, the antibody undergoing antigen-antibody reaction with human NF-κB-p65/RelA in which 254th amino acid threonine is phosphorylated but not undergoing antigen-antibody reaction with human NF-κB-p65/RelA in which 254th amino acid threonine is not phosphorylated.

Effects of the Invention

By the present invention, means by which the probability that a prostate cancer will metastasize can be determined at an early stage was first provided. By the present invention, since the probability that a prostate cancer will metastasize can be determined at an early stage, therapy or treatment of the patient can be properly selected, so that the present invention is expected to greatly contribute to the therapy of prostate cancer.

BEST MODE FOR CARRYING OUT THE INVENTION

Figure 1:
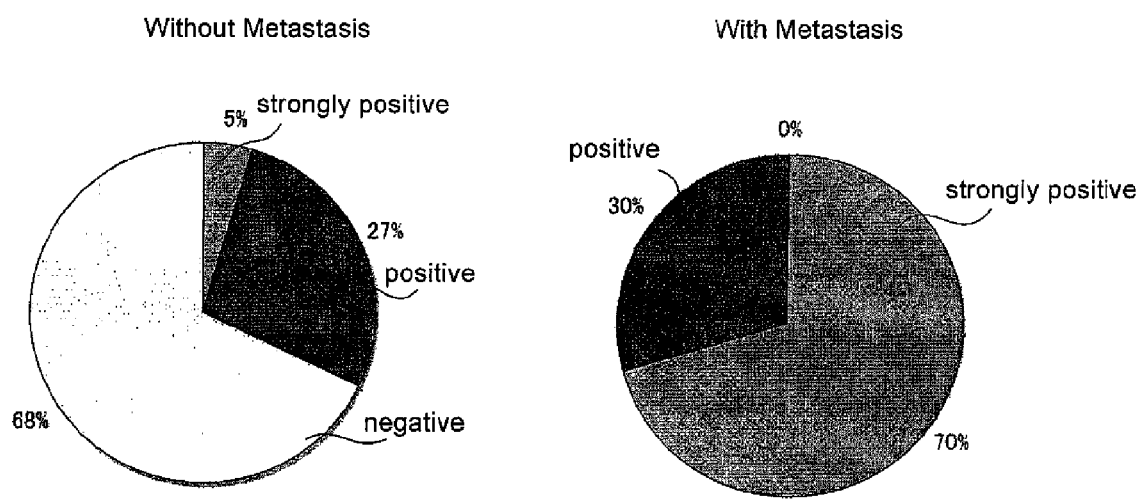
FIG. 1 A FIGURE which comparatively shows the ratio of strongly positive, positive and negative results of immunohistochemical staining of prostate tissues in the cases where bone metastasis was observed and not observed, respectively, which immunohistochemical staining was carried in the Example of the present invention.

NF-κB is a transcription factor which is expressed widely in most cells. Since it is expressed in nuclei of cells, it is called nuclear factor. NF-κB-p65/RelA is one of the subunits of NF-κB. The amino acid sequence of human NF-κB-p65/RelA and the cDNA sequence encoding it are known, and are shown in GenBank Accession No. M62399. The base sequence of the cDNA of human NF-κB-p65/RelA and the amino acid sequence encoded thereby are shown in SEQ ID NO: 1 in SEQUENCE LISTING, and the amino acid sequence alone is shown in SEQ ID NO:2.

In the method of the present invention, the human NF-κB-p65/RelA in which 254th amino acid threonine is phosphorylated (hereinafter also referred to as "254 phosphorylated NF-κB-p65/RelA" for convenience). The term "threonine is phosphorylated" means that the hydroxyl group in the side chain of threonine is converted to a phosphoric acid ester. Phosphorylated threonine per se is well-known. In the present invention, the term "measure" includes any of detection, semi-quantification and quantification. The term "measure the 254 phosphorylated NF-B-p65/RelA" means to measure the 254 phosphorylated NF-κB-p65/RelA distinctly from the NF-κB-p65/RelA whose 254th threonine is not phosphorylated (hereinafter also referred to as "254 unphosphorylated NF-κB-p65/RelA" for short).

An example of the preferred method for measuring the 254 phosphorylated NF-κB-p65/RelA is an immunoassay using an antibody (hereinafter also referred to as "254 phosphorylated NF-κB-p65/RelA-specific antibody") or an antigen-binding fragment thereof, which antibody undergoes antigen-antibody reaction with 254 phosphorylated NF-κB-p65/RelA but does not undergo antigen-antibody reaction with 254 unphosphorylated NF-κB-p65/RelA.

The 254 phosphorylated NF-κB-p65/RelA-specific antibody may be a polyclonal antibody or a monoclonal antibody. The 254 phosphorylated NF-κB-p65/RelA-specific polyclonal antibody can be obtained by preparing a polyclonal antibody by a conventional method using as an immunogen 254 phosphorylated NF-κB-p65/RelA or a fragment thereof containing the 254th threonine; and removing, from the obtained polyclonal antibody, by adsorption the antibodies which also undergo antigen-antibody reaction with 254 unphosphorylated NF-κB-p65/RelA (see the Example below). The monoclonal antibody can be obtained by preparing hybridomas each producing an anti-254 phosphorylated NF-κB-p65/RelA monoclonal antibody by a conventional method using as an immunogen 254 phosphorylated NF-κB-p65/RelA or a fragment thereof containing the 254th threonine; selecting, from the obtained hybridomas, those producing the 254 phosphorylated NF-κB-p65/RelA-specific antibody; culturing the selected hybridomas in vitro or in abdominal cavity of an animal, or the like; and recovering the 254 phosphorylated NF-κB-p65/RelA-specific antibody produced by the hybridomas from the culture medium or ascites. In the immunoassay, the 254 phosphorylated NF-κB-p65/RelA-specific antibody may be used, or a fragment thereof having a binding activity to the antigen, such as Fab fragment or F(ab')$_2$ fragment (in the present invention, referred to as "antigen-binding fragment") may also be used.

As the immunogen used for the preparation of the anti-254 phosphorylated NF-κB-p65/RelA antibody, the whole molecule of 254 phosphorylated NF-κB-p65/RelA or a fragment thereof containing the 254th threonine may be used, as mentioned above. In the latter case, the size of the peptide fragment is preferably not less than 10 amino acids, more preferably not less than 12 amino acids. Since a 254 phosphorylated NF-κB-p65/RelA-specific antibody was obtained in the Example described below using a fragment having 12 amino acids ((VFRT(PO3H2)PPYADPSC) (SEQ ID NO: 3), the "(PO3H2)" after T means that the hydroxyl group in the side chain of this threonine (T) is phosphorylated), a size of 12 amino acids is sufficient. Needless to say, however, those having a longer size (the longest is the whole molecule of 254 phosphorylated NF-κB-p65/RelA) can also be used as the immunogen. The peptide fragment of the 254 phosphorylated NF-κB-p65/RelA which can be used as the immunogen can easily be chemically synthesized using a commercially available peptide synthesizer. Since the phosphorylated threonine per se is commercially available, a peptide fragment containing the phosphorylated threonine as the 254th threonine can be synthesized by using the commercially available threonine as a material in the step of binding the 254th threonine when the peptide is chemically synthesized. In cases where a peptide fragment is used as the immunogen, the peptide fragment may be used as the immunogen as it is, or the peptide fragment bound to a protein carrier such as bovine serum albumin, casein or keyhole limpet hemocyanin, may be used as the immunogen. Since a 254 phosphorylated NF-κB-p65/RelA-specific antibody was obtained in the Example below by administering a peptide fragment consisting of 12 amino acids as it is, binding to the carrier protein is not indispensable.

The immunoassay can be carried out by immunohistochemical staining to a prostate tissue separated from the living body, or by a well-known immunoassay such as sandwich method, competition method or agglutination method using as a test sample a cell homogenate of a prostate tissue separated from the living body or the purified or partially purified product thereof containing NF-κB-p65/RelA. Among these methods, immunohistochemical staining is preferred. The immunohistochemical staining can be carried out by a conventional method except that the 254 phosphorylated NF-κB-p65/RelA-specific antibody is used as the antibody (see the Example below). Since a kit for immunohistochemical staining is commercially available, the immunohistochemical staining can be easily carried out using the commercially available kit and the above-described 254 phosphorylated NF-κB-p65/RelA-specific antibody as the antibody.

As will be concretely described in the Example below, in the prostate cancer tissue metastasized to bone, the percentage that the reactivity with the 254 phosphorylated NF-κB- p65/RelA-specific antibody is positive (positive rate) was statistically significantly higher than in the cases where bone metastasis was not observed. Moreover, among the cases where the 254 phosphorylated NF-κB-p65/RelA was positive, in the cases where the abundance of 254 phosphorylated NF-κB-p65/RelA was especially high (in the cases where the immunohistochemical staining was strongly positive), the percentage of bone metastasis was especially high. Further, in most cases where bone metastasis occurred, the immunohistochemical staining was positive irrespective of the histological malignancy (Gleason grade). These results show that the 254 phosphorylated NF-κB-p65/RelA can be utilized as a prostate cancer metastasis marker indicating the probability of metastasis of prostate cancer, and whether metastasis will occur in the future or not can be estimated irrespective of the histological malignancy.

The present invention will now be described more concretely by way of an example thereof. However, the present invention is not restricted to the Example below.

EXAMPLE

Materials and Methods

1. Preparation of 254 Phosphorylated NF-κB-p65/RelA-Specific Antibody

A phosphorylated peptide (VFRT(PO3H2)PPYADPSC) (SEQ ID NO: 3) which was a fragment of p65/RelA, containing the 254th threonine (12 amino acids from the 251st valine to 262nd cystein) wherein the 254th threonine had a phosphate group attached thereto was chemically synthesized using a peptide synthesizer. As the phosphorylated threonine to which a phosphate group was added, a commercially available product was used. The obtained peptide fragment was mixed with an equal amount of Freund complete adjuvant (first immunization) or Freund incomplete adjuvant (second and subsequent immunization), and an emulsion was prepared by sonication. The resulting viscose emulsion was subcutaneously administered to the back of a rabbit (New Zealand white rabbit). The immunization was conducted totally 4 times at 2-week intervals. At the time of third immunization, a small amount of the antigen protein was sampled, and antibody titer was measured by ELISA. Two weeks after the fourth immunization, the total blood was collected from the carotid artery under anesthesia with ketamine-xylazine. The collected blood was left to stand at room temperature for 1 hour, and then at 4° C. overnight, followed by centrifugation at 3000 rpm for 10 minutes to obtain a serum.

Using a commercially available antibody-purification kit (Amersham Bio., HiTrap Protein A HP), antibody was purified from the obtained antiserum. The buffers used were as follows:

| Binding buffer | 20 mM sodium phosphate, pH 7.0 |
| Elution buffer | 0.1 M sodium citrate, pH 3.0 |
| Neutralization buffer | 1.0 M Tris-HCl, pH 9.0 |

Concrete purification operation was as follows:
(1) Preparation of column: A syringe was connected without introducing bubbles into the column, and 25 mL of ultrapure water was applied at a rate of 5 drops/second.
(2) Equilibration of Column: 25 mL of binding buffer was applied at a rate of 5 drops/second.
(3) Addition of sample: The prepared sample (dilution of antiserum) was applied at a rate of 5 drops/second, and the adsorbed components were washed, followed by application of 25 mL of binding buffer at a rate of 5 drops/second.
(4) Elution of antibody: 25 mL of elution buffer was applied at a rate of 5 drops/second, the eluted solution was collected in 3 mL fractions (300 μL of neutralization buffer was added to each collection tube), the concentration of each of the eluted fractions was measured, the absorbance at 280 nm of each fraction was measured, the antibody fraction was recovered and dialyzed to PBS(−) overnight to exchange the buffer.

From the obtained polyclonal antibody, the antibody which underwent antigen-antibody reaction also with 254 unphosphorylated NF-κB-p65/RelA was removed by adsorption. More particularly, a biotinylated 254 unphosphorylated NF-κB-p65/RelA (VFRTPPYADPSC) (SEQ ID NO: 3) chemically synthesized with a peptide synthesizer was bound to commercially available streptavidin-magnetic beads (amount of total bound antigen: 0.01 mg; amount of beads: 0.2 mg), and the beads were mixed with 10-fold diluted antibody solution (0.3 mL) at 4° C. for 2 hours.

Then the non-specific antibody adsorbed to the unphosphorylated peptide was removed using a magnet, and the supernatant was recovered to obtain a 254 phosphorylated NF-κB-p65/RelA-specific antibody.

2. Immunohistochemical Staining

Using a commercially available immunohistochemical staining kit (VECTASTAIN ABC Kit), immunohistochemical staining with the 254 phosphorylated NF-κB-p65/RelA-specific antibody obtained in the above-described 1 was performed on prostate tissues separated from patients. The concrete operation of the immunohistochemical staining was as follows:
(1) Deparaffinization and hydrophilization of each tissue section with xylene and ethanol
(2) Washing twice (each for 5 minutes) with 100 mL each of Tris buffered physiological saline (TBS).
(3) Inactivation of endogenous peroxidase (1 hour) with 60 mL of TBS supplemented with 2 mL of 30% $H_2O_2$ (1%)
(4) Washing twice (each for 5 minutes) with 100 mL each of TBS.
(5) Blocking (1 hour) with goat serum in TBS (3 mL) (final concentration: 10%)
(6) Washing once (for 5 minutes) with 100 mL of TBST (0.1% Tween 20 (trade name)-containing TBS)
(7) Primary antibody (254 phosphorylated NF-κB-p65/RelA-specific antibody prepared in the above-described 1) diluted (50-fold to 150-fold) with the blocking solution was added to the sample and the resultant was left to stand at room temperature for 2 hours or at 4° C. overnight.
(8) Washing twice (each for 5 minutes) with 100 mL each of TBS
(9) Secondary antibody (500 μL of TBS supplemented with 2 μL of biotinylated secondary antibody (goat anti-rabbit IgG antibody, included in the kit)) was added to the sample and the resultant was allowed to react for 2 hours.
(10) Washing twice (each for 5 minutes) with 100 mL each of TBS
(11) Preparation of AB solution (10 mL of TBS supplemented with 2 drops each of A: avidin solution (C solution) and B: biotinylated peroxidase (D solution). AB solution was prepared 30 minutes before use and allowed to react.
(12) AB solution is added to the sample, and the resultant is allowed to react for 2 hours.
(13) Washing twice (each for 5 minutes) with 100 mL each of TBS
(14) DAB solution (TBS (5 mL) containing 50 μg (10 μg/mL) of diaminobenzidine (DAB) which is a substrate of peroxidase and 5 μL (0.03%) of $H_2O_2$ (produced by VECTOR) is added to the sample, and the resultant is allowed to react for about 5 to 10 minutes in the dark. Coloring is checked sometimes.
(15) Washing once (for 5 minutes) with 100 mL of TBS
(16) Staining of nuclei of cells in blue with hematoxylin reagent
(17) Ethanol substitution, dropping xylene and a sealant, and seal with a cover glass 3. Materials Prostate cancer operation samples extirpated in Yokohama City University Hospital and related hospitals and pre-operation needle biopsies (total 49 cases, breakdown was as follows:)
Cases where bone metastasis occurred within 3 to 5 years (27 cases)
Cases where bone metastasis did not occur in the period mentioned above (22 cases)
Bone metastatic site samples of prostate cancer (6 cases)

4. Results

Immunostaining was performed on the prostate cancer tissue samples by immunohistochemistry with the antibody. The samples used were the needle biopsy tissue samples or the extirpated prostate samples of the cases (27 cases) where bone metastasis occurred during the follow-up period of 3 to 5 years (including the cases where bone metastasis was found at the first visit), and the cases (22 cases) where bone metastasis did not occur during the above-mentioned period. Bone metastatic site samples of prostate cancer (6 cases) were also stained, and evaluation at the metastatic site was also conducted.

As a result of immunohistochemical staining, in prostate cancer cases where bone metastasis occurred, positive image (brown) was observed in the primary focus and in the metastatic focus in the prostate cancer cells. In the staining pattern, strong staining was observed chiefly in the nuclei. Further, irrespective of histological malignancy (Gleason grade), in most of the bone metastasis cases, the results were positive and in most of the cases where bone metastasis did not occur, the results were negative.

The results of staining were classified into 3 grades, namely, negative, positive, and strongly positive by two or more pathologists. The negative grade was the cases where staining with the antibody was not observed; the strongly positive grade was the cases where strong staining with the antibody was observed; and the positive grade was the cases where staining with the antibody was observed, but the degree of staining was not so strong as the strongly positive grade.

The results are shown in Table 1 below and FIG. 1. As shown in Table 1 and FIG. 1, irrespective of the histological malignancy, in the cases where bone metastasis occurred, 19 cases were strongly positive grade, 8 cases were positive grade and 0 case was negative grade, so that the antibody reaction was positive in 100% of the cases. On the other hand, in the cases where bone metastasis did not occur, 1 case was strongly positive grade, 6 cases were positive grade and 15 cases were negative grade, so that most of them was negative grade. Since the follow-up period is short, it is thought that there is a possibility that in the strongly positive case and the positive cases in the cases where bone metastasis did not occur, bone metastasis may occur in the future. Further, in the site of bone metastasis, among the 6 cases, 3 cases were strongly positive grade and 3 cases were positive grade, so that the positive rate was 100% too. To determine whether there is a significant difference between the groups with bone metastasis and without bone metastasis in the results of staining with the antibody, a statistical test (chi square test) was carried out. As a result, in the bone metastasis-positive group, the staining with the antibody was significantly strongly positive or positive with a 99% significant difference ($P<0.01$ ($\chi_0 2=31.2>\chi 2(2; 0.01)=9.21$). By these results, it was proved that the antibody can be used as a molecular marker (diagnostic reagent) for determining the probability that the prostate cancer will metastasized.

TABLE 1

| Immunohistochemical Staining | Number of Cases | |
|---|---|---|
| | without metastasis | with metastasis |
| Strongly Positive | 1 | 19 |
| Positive | 6 | 8 |
| Negative | 15 | 0 |
| Total | 22 | 27 |

The invention claimed is:

1. A method for determining probability that a prostate cancer will metastasize, said method comprising measuring human NF-κB-p65/RelA in which 254th amino acid threonine is phosphorylated, said human NF-κB-p65/RelA being contained in a prostate tissue separated from human, wherein an increase in the levels of human NF-κB-p65/RelA in which the 254th amino acid threonine is phosphorylated in a patient compared to the levels of human NF-κB-p65/RelA in which the 254th amino acid threonine is phosphorylated in patients not having metastasized prostate cancer indicates an increase in the probability that a prostate cancer will metastasize.

2. The method according to claim 1, carried out by an immunoassay using an antibody or an antigen-binding fragment thereof, said antibody undergoing antigen-antibody reaction with human NF-κB-p65/RelA in which 254th amino acid threonine is phosphorylated but not undergoing antigen-antibody reaction with human NF-κB-p65/RelA in which 254th amino acid threonine is not phosphorylated.

3. The method according to claim 2, wherein said immunoassay is immunohistochemical staining.

4. The method according to according to any one of claims 1 to 3, wherein the metastasis is bone metastasis.

* * * * *